(12) United States Patent
Woolfenden et al.

(10) Patent No.: US 6,564,656 B1
(45) Date of Patent: May 20, 2003

(54) SAMPLING DEVICE

(75) Inventors: Elizabeth Angela Woolfenden, Bridgend (GB); Alun Cole, Brisgend (GB)

(73) Assignee: Markes International Limited, Pontyclun (GB)

( * ) Notice: Subject to any disclaimer, the term of this patent is extended or adjusted under 35 U.S.C. 154(b) by 0 days.

(21) Appl. No.: 09/501,821

(22) Filed: Feb. 10, 2000

Related U.S. Application Data

(63) Continuation-in-part of application No. 09/310,494, filed on May 12, 1999, now abandoned.

(30) Foreign Application Priority Data

May 19, 1998 (GB) .............................................. 9810593
Dec. 22, 1999 (GB) .............................................. 9930125

(51) Int. Cl.⁷ ................................................. G01N 1/00
(52) U.S. Cl. ................................................. 73/863.21
(58) Field of Search ........................ 73/863.11, 863.12, 73/863.21, 863.23, 864.34, 864.51, 864.52, 864.73, 864.01, 864.91, 707; 220/367.1, 373, 374; 422/102

(56) References Cited

U.S. PATENT DOCUMENTS

| | | | | | |
|---|---|---|---|---|---|
| 3,915,008 | A | * | 10/1975 | Silverman et al. | ............ 73/707 |
| 4,046,014 | A | * | 9/1977 | Boehringer et al. | ...... 73/863.12 |
| 4,790,857 | A | * | 12/1988 | Miksch | ..................... 73/864.51 |
| 5,231,874 | A | * | 8/1993 | Gilbert | ......................... 73/707 |
| 5,343,754 | A | * | 9/1994 | Stone | ........................... 73/707 |
| 5,482,677 | A | * | 1/1996 | Yao et al. | ................. 73/863.21 |
| 5,574,230 | A | * | 11/1996 | Baugh | ..................... 73/863.21 |

FOREIGN PATENT DOCUMENTS

| | | |
|---|---|---|
| EP | 0051288 A1 | 5/1982 |
| EP | 0453434 A1 | 10/1991 |
| GB | 875065 | 8/1961 |

* cited by examiner

*Primary Examiner*—Robert Raevis
(74) *Attorney, Agent, or Firm*—Edwin D. Schindler

(57) ABSTRACT

A sampling device containing an adsorbing material and fitted with a cap formed with an elongate passage through which gases may pass into and out of the device. When fitted to the device, the elongate passage in the cap effectively seals the device, requiring a flow of gas to be driven through the device to obtain a sample therefrom.

9 Claims, 2 Drawing Sheets

SAMPLING DEVICE

This is a continuation-in-part of application Ser. No. 09/310,494, filed May 12, 1999, now abandoned.

FIELD OF THE INVENTION

The present invention relates to a sampling device used to sample ambient atmospheres.

BACKGROUND OF THE INVENTION

It is known to provide a sampling device in the form of a tube containing an adsorbing material. One end of the tube is normally closed by a tightly-fitting cap which is temporarily removed to sample the ambient atmosphere at a test location, and then replaced to prevent subsequent contamination of the sample.

Later, at an analysis site, the tightly-fitting cap is once again removed from the tube and is replaced by a more loosely-fitting cap. The sampling device is then loaded into a hopper for processing by an analytical instrument.

The loosely-fitting cap, whilst providing a worse seal than the tightly-fitting cap, is necessary to allow the cap to be removed by an automatic mechanism within the analytical instrument so that the contents of the sampling device may be analysed.

With the loosely-fitting cap removed, the contents of the sampling device are analysed by heating the adsorbing material to release therefrom any volatile organic compounds (VOCs) that may have been adsorbed during the sampling period, the desorbed VOCs being driven from the tube and into the analytical instrument by a flow of inert gas.

However, the process described above has a number of serious drawbacks. Firstly, the manual removal of the tightly-fitting cap is both difficult and time consuming. Secondly, as mentioned above, the loosely-fitting cap provides a poor seal which may allow a sample to become contaminated. Thirdly, the provision of an automatic cap-removal mechanism significantly increases the cost and complexity of the analytical instrument.

SUMMARY OF THE INVENTION

We have now devised an arrangement which overcomes the limitations of existing sampling devices.

According to a first aspect of the present invention, there is provided a sampling device containing an adsorbing material and fitted with a cap formed with at least one elongate passage through which gases may pass into and out of the device.

Preferably the cap is formed, at one end, with a socket to receive a connecting portion of the sampling device. Preferably the cap is a sliding fit over said connecting portion. Preferably the socket is provided internally with one or more 'O'-ring seals for embracing the outer surface of said connecting portion.

When tightly fitted to the sampling device at a test site following a sampling period, the elongate passage through the cap thus limits the rate at which gases may subsequently diffuse into or out of the device, but, at the same time, allows desorbed VOCs to be driven out of the device by a flow of gas for analysis.

Two major factors govern the optimum dimensions of the bore formed by the or each passage through the cap.

Firstly, the uptake of VOCs by the adsorbing material is governed by Fick's Law, which states that the rate of uptake Q of a particular VOC is proportional to the cross sectional area A of the bore, and is also inversely proportional to length of the bore, more particularly $$Q = \frac{DA}{L}t$$

Where Q is the uptake quantity, D is the diffusion constant for a particular VOC, t is the duration of exposure, A is the cross-sectional area of the bore and L is the diffusion length.

Thus the rate of uptake may be controlled by varying either the diameter or the length of the bore.

However, there is a practical limit on the minimum diameter of the bore, which is determined by the maximum acceptable pressure difference p between the ends of the bore as inert gas is driven through the bore during analysis.

The pressure difference p between the ends of the bore is governed by Poiseuille's equation which states that the pressure difference p is proportional to the length of the bore L and to the volume of gas flow V through the bore, and is also inversely proportional to the radius of the bore raised to the power 4, more specifically $$V = \frac{r^4 \pi}{L 8 \eta} p$$

Where V is the volume of gas passing through the bore, r is the radius of the bore, L is the length of the bore, p is the pressure difference between the ends of the bore and $\eta$ is the coefficient of viscosity of the gas.

So as not to exceed a maximum acceptable pressure drop, the minimum diameter of the bore must therefore be limited. Once this limit has been reached, any further reduction in the rate of uptake of VOCs can only be achieved by increasing the length of the bore.

One or more bores may be formed by respective passages which extend axially through the cap.

In this case, the or each passage is preferably provided by the bore of a respective capillary tube fitted into a bore through the cap. Preferably the passage has a length at least 10 times (more preferably 20 times) its width. For example, the passage may have a diameter of 0.01 inch (0.25 mm) and a length of 12 mm.

However, we have found that to provide the low rates of uptake required in most modern sampling applications, whilst maintaining a preferred pressure drop of around 1 psi for gas flows of up to 100 ml/min, a bore length far exceeding that achievable by means of an axial passage is typically required.

In order to provide a long bore within the dimensional confines of a conventional cap, at least one convoluted passage is preferably formed through the cap.

The or each convoluted passage may, for example, be provided by a respective helical tube disposed within a hollow compartment of the cap.

However, more preferably, the cap comprises a sleeve and a cylindrical insert, with one or other of the opposed surfaces of the sleeve and the insert being formed with at least one helical channel such that, when the insert is fitted into the sleeve, the or each helical channel forms a respective passage through which gases may pass into and out of the device.

According to a second aspect of the present invention, there is provided a cap comprising a sleeve and a cylindrical insert, one or other of the opposed surfaces of the sleeve and the insert being formed with at least one helical channel such that, when the insert is fitted into the sleeve, the or each helical channel forms a respective passage through which gases may pass into and out of the device.

According to a third aspect of the present invention, there is provided a method of analysing a sample held within sampling device, the method comprising the steps of fitting at least one cap of the type defined above to the sampling device following a sampling period, and offering the sampling device to an analytical instrument which provides a flow of gas through the sampling device to drive said sample out of the device through the cap.

Preferably two caps of the type defined above are fitted to the sampling device with said flow of gas being introduced into the device through the passage or passages formed in one of the caps to drive said sample out of the device through the passage or passages formed in the other cap.

According to a fourth aspect of the present invention, there is provided a sampling device having a tubular opening and a cylindrical insert, one or other of the opposed surfaces of the tubular opening and the insert being formed with at least one helical channel such that, when the insert is inserted into the opening, the or each channel forms a respective passage through which gases may pass into and out of the device.

According to a fifth aspect of the present invention, there is provided a method of analysing a sample held within a sampling device having a tubular opening, the method comprising the steps of fitting a tubular insert into the opening following a sampling period, and offering the sampling device to an analytical instrument which provides a flow of gas through the sampling device to drive said sample out of the device through at least one passage formed by a respective helical channel formed in one or other of the opposed surfaces of the tubular opening and the insert.

Preferably the device comprises two openings, each fitted with a respective insert, said flow of gas being introduced into the device through the passage or passages formed in one of the openings to drive said sample out of the device through the passage or passages formed in the other opening.

BRIEF DESCRIPTION OF THE DRAWINGS

Embodiments of the present invention will now be described by way of examples only and with reference to the accompanying drawings, in which.

DETAILED DESCRIPTION OF THE DRAWINGS

Figure 1:
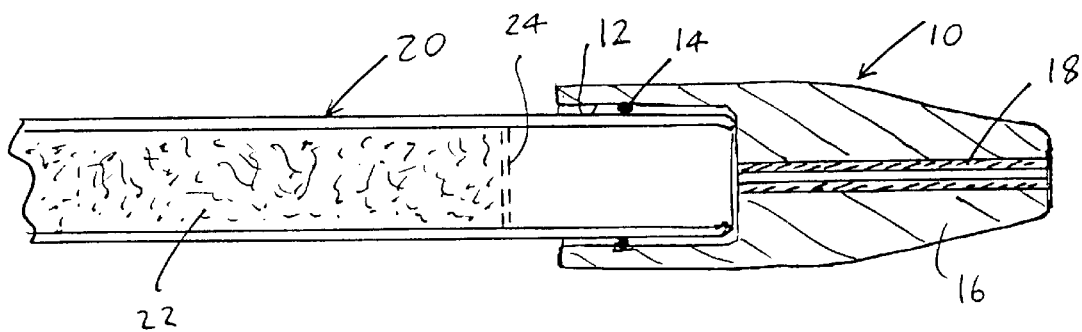
FIG. 1 is a longitudinal section through the first embodiment of end-cap in accordance with the present invention.

Referring to FIG. 1 of the drawings, a sampling device is shown comprising a cap 10 slidably fitted to one end of a sample tube 20: a similar cap is also fitted to the opposite end of the tube. The sample tube 20 is open at both ends and contains a quantity of adsorbent material 22 which is held in place between two screens e.g. of stainless steel gauze spaced from the respective ends of the tube 20, one such screen being shown at 24. The cap 10 comprises a tubular rigid body formed at one end with a cylindrical socket 12 fitted internally with an 'O'-ring seal 14: the cap is thus arranged to fit over the end of the sample tube 20 with the seal 14 embracing the outer surface of the sample tube. The socket 12 extends only part-way along the cap 10 and accordingly the cap has a substantial portion 16 which extends outwardly beyond the end of the sample tube 20: in the example shown, the length of the socket 12 is 12 mm and the length of the remaining, outwardly-projecting portion 16 is at least 12 mm. A fine bore extends axially through the portion 16, from the inner end of the socket 12 to the extreme outer end of the cap: this bore is provided by a nickel capillary tube 18, of 0.01 inch inner diameter, fitted into a bore through the cap (which may be of stainless steel).

In use of the device to take a sample, the cap 10 is removed from one end of the tube 20 to allow the ambient atmosphere to diffuse, or be pumped by means of a suitable pump, into the adsorbent through that open end of the tube. After a predetermined sampling period, the cap 10 is replaced and the sample tube, thus effectively sealed, is taken to a laboratory for analysis.

It will be appreciated that whilst the sample tube is closed by its pair of caps, negligible diffusion of air or gas into the adsorbent 22 will take place, because of the extended length and small diameter of the passage 18 provided through the cap. The cap thus serves to seal the sample tube both prior to the sampling period, and between the end of the sampling period and the analysis process.

However, during the analysis process, it is unnecessary to remove either of the caps from the sample tube. Thus, the sample tube can be offered to an automatic analytical instrument, in which the caps of the opposite ends of the sample tube are automatically coupled to the ends of flow ducts, enabling the apparatus to provide a flow of inert gas through the sample tube, via the fine bore in each of its caps. The apparatus will include a heater to heat the tube and thus liberate volatile substances adsorbed by the adsorbent material 22, the liberated substances being carried by the through-flowing gas to the analytical elements of the instrument.

In some cases it may be desirable, after the sampling, to seal the sample tube with blanking caps (i.e. imperforate caps): this is especially if there is expected to be a long time delay between the sampling and analysis. These blanking caps are then removed, and replaced with the diffusion-limiting caps of the present invention, before the sample tube is introduced into the automatic analysing apparatus.

As explained above, to limit the rate of uptake of VOCs by the device to the extent required in many modern sampling applications, it is sometimes necessary to provide a very long passage in the each of the end caps.

Figure 2:
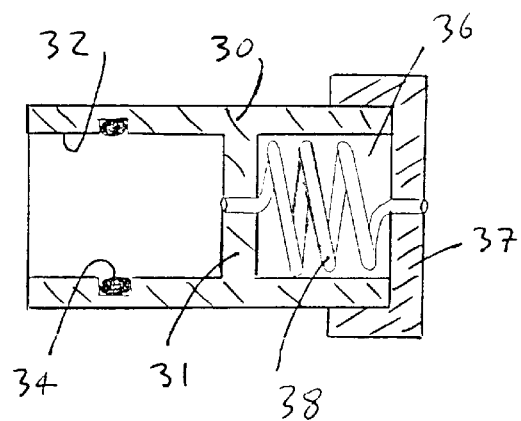
FIG. 2 is a longitudinal section through a second embodiment of end-cap in accordance with the present invention.

One way in which this object may be achieved according to the present invention is to fit a cap of the type shown in FIG. 2 to one or both ends of a sampling tube.

The cap of FIG. 2 comprises a tubular body 30 formed with a partition wall 31 at a point intermediate its opposite ends. The body is thus formed with a socket 32 at one end, provided internally with an 'O'-ring seal 34, to fit over an end of a sample tube. At its other end, the cap body 30 is formed with a hollow compartment 36 which has a cup-shaped closure 37 fitted over it: a capillary tube 38, which is wound into a helical shape, is positioned within the compartment 36 with its opposite ends passed through the partition wall 31 and the closure 37.

It will be appreciated that the cap of FIG. 2 may be used in the same way as the cap 10 of FIG. 1, the helical tube 38 providing an extended diffusion-limiting passage into the sample tube.

Figure 3:
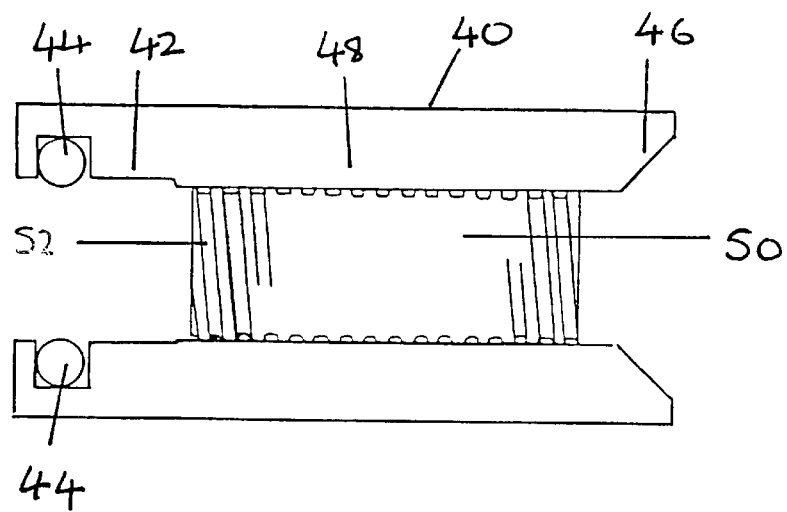
FIG. 3 is a side view of a third embodiment of end-cap in accordance with the present invention.

Alternatively a cap of the type shown in FIG. 3 may be fitted to one or both ends of a sampling tube. The cap of FIG. 3 comprises a sleeve 40 having an end portion 42 of increased internal diameter and fitted with an O-ring seal 44 for securing the cap to the open end of a sampling tube. The opposite end of the sleeve 40 has a tapered entrance portion 46 for attachment to an analytical instrument.

An intermediate portion 48 of the sleeve 40 is fitted with a cylindrical insert 50, the surface of the insert being formed with a helical channel 52 along its length.

In use, the helical channel 52 in the or each cap forms a passageway for communicating gases between the interior and the exterior of the tube to which it is fitted.

Figure 4:
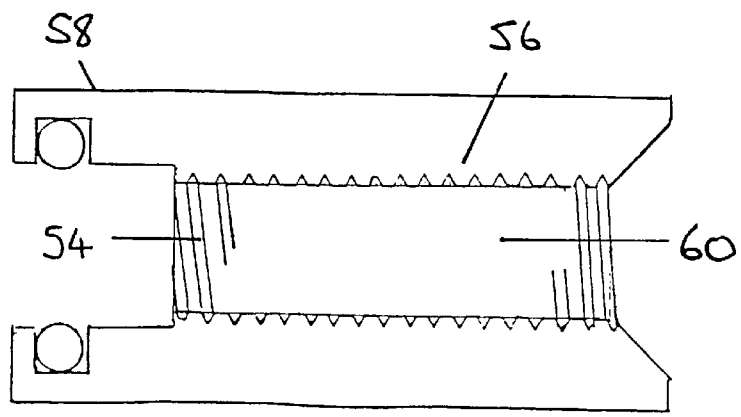
FIG. 4 is a side view of a fourth embodiment of end-cap in accordance with the present invention.

A further alternative would be to fit a cap of the type shown in FIG. 4 to one or both ends of a sampling tube. The cap of FIG. 4 differs from that of FIG. 3 in that a helical channel 54 is formed along an interior surface portion 56 of the sleeve 58 rather than along the surface of the insert 60.

It will be appreciated that the rate of uptake of VOCs into a tube to which either cap is fitted is determined by the cross-sectional profile, pitch and number of the or each helical channels formed in the sleeve or in the insert of the cap, and by the length of the insert, the latter being readily varied by trimming the insert to an appropriate length.

Figure 5:
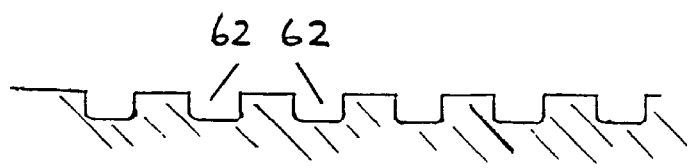
FIG. 5 is a section through a portion of the channelled surface of the insert of FIG. 3.

A preferred rectangular channel profile is shown in FIG. 5, in which successive turns 62 of the channel are spaced apart to minimise leakage between those turns.

The channel formed in the sleeve or in the insert of a cap is preferably cut respectively using an appropriately formed tap or die.

Caps may be supplied without channels, allowing the purchaser to form one or more channels in the tubular part or in the insert to his own requirements.

Caps may instead be supplied together with an assortment of interchangeable inserts each having a different length, cross-sectional channel profile, channel pitch and or number of channels.

It would also remain in accordance with the present invention for inserts to be fitted directly into the opposite ends of a sample tube.

The arrangements thus described provide a convenient means for obtaining and processing atmospheric samples.

What is claimed is:

1. A method of analysing a sample held within a sampling device having a tubular opening, the method comprising the steps of fitting a tubular insert into said opening following a sampling period, and offering said sampling device to an analytical instrument which provides a flow of gas through said device to drive said sample out of said device through at least one passage formed by a respective helical channel formed in one or other of the opposed surfaces of said tubular opening and said insert.

2. A method as claimed in claim 1, wherein said device comprises two openings, each fitted with a respective insert, said flow of gas being introduced into said device through the said passage or passages formed in one of said openings to drive said sample out of said device through the said passage or passages formed in the other opening.

3. A sampling device comprising an adsorbing material and fitted with a cap formed with at least one elongate passage following a helical path through which gases are passable into, and out of, said sampling device.

4. The sampling device according to claim 3, wherein said cap comprises a sleeve and a cylindrical insert, with said sleeve and said cylindrical insert having opposed surfaces and with one of the opposed surfaces of said sleeve or said cylindrical insert being formed with at least one helical channel, so that when said cylindrical insert is fitted into said sleeve, said at least one helical channel forms a respective passage through which gases are passable into, and out of, said sampling device.

5. A sampling device comprising an adsorbing material and fitted with a cap formed with at least one elongate passage following a convoluted path through which gases are passable into, and out of, said sampling device, said at least one elongate passage being provided by a tube disposed within a hollow compartment formed in said cap.

6. A sampling device comprising an adsorbing material and fitted with a cap formed with at least one elongate passage extending axially through said cap through which gases are passable into, and out of, said sampling device, said at least one elongate passage being provided by a bore of a respective capillary tube fitted into a bore through said cap.

7. A method for analyzing a sample held within a sampling device, said method comprising the steps of:

fitting at least one cap to said sampling device following a sampling period, said at least one cap being formed with at least one elongate passage following a helical path through which gases are passage into, and out of, said sampling device; and, offering said sampling device to an analytical instrument providing a flow of gas through said sampling device for driving the sample out of said sampling device through said cap.

8. The method for analyzing a sample held within a sampling device according to claim 7, wherein said fitting step includes fitting two caps to said sampling device, each cap of said two caps being formed with at least one elongate passage through which gases are passable into, and out of, said sampling device, said flow of gas being introduced into said sampling device through said at least one elongate passage formed in a first cap of said two caps for driving the sample out of said sampling device through said at least one elongate passage formed in a second cap of said two caps.

9. A sampling tube, comprising:

a tubular opening; and, a cylindrical insert, with said tubular opening and said cylindrical insert having opposed surfaces and with one of the opposed surfaces of said tubular opening or said cylindrical insert being formed with at least one helical channel, so that when said cylindrical insert is inserted into said tubular opening, said at least one helical channel forms a respective passage through which gases are passable into, and out of, said sampling tube; and, an adsorbing material for testing a sample contained in said sampling tube.

* * * * *